(12) United States Patent
Shida et al.

(10) Patent No.: US 7,638,132 B2
(45) Date of Patent: Dec. 29, 2009

(54) HIGHLY SAFE SMALLPOX VACCINE VIRUS AND VACCINIA VIRUS VECTOR

(75) Inventors: Hisatoshi Shida, Hokkaido (JP); Minoru Kidokoro, Tokyo (JP)

(73) Assignee: National University Corporation Hokkaido University, Sapporo-Shi (JP)

( * ) Notice: Subject to any disclaimer, the term of this patent is extended or adjusted under 35 U.S.C. 154(b) by 83 days.

(21) Appl. No.: 10/581,495

(22) PCT Filed: Dec. 5, 2003

(86) PCT No.: PCT/JP03/15632

§ 371 (c)(1), (2), (4) Date: Jan. 26, 2007

(87) PCT Pub. No.: WO2005/054451

PCT Pub. Date: Jun. 16, 2005

(65) Prior Publication Data

US 2007/0298054 A1    Dec. 27, 2007

(51) Int. Cl.
*A61K 39/285* (2006.01)
*C12N 7/00* (2006.01)
*C12N 7/01* (2006.01)
*C12N 15/863* (2006.01)

(52) U.S. Cl. .............. 424/199.1; 424/232.1; 435/235.1; 435/320.1

(58) Field of Classification Search ........................ None
See application file for complete search history.

(56) References Cited

FOREIGN PATENT DOCUMENTS

WO    WO-90/12101 A    10/1990
WO    WO 2004/087047    * 10/2004

OTHER PUBLICATIONS

Mathew et al, Journal of General Virology 82:1199-1213 (2001) (cited in IDS filed Sep. 6, 2006).*
Engelstad et al (Virology 194:627-637, 1993) (cited in IDS).*
Takahashi-Nishimaki et al (Virology 181:158-164, 1991).*
Sugimoto et al (Vaccine 12:675-681, 1994).*
Smith et al (Journal of General Virology 83:2915-2931, 2002).*
Cohen (Science 298:2314, 2002).*
Katz et al (AIDS Research and Human retroviruses 13:1497-1500, 1997) (cited in IDS).*
Kidokoro et al (Microbes and Infection 4:1035-1044, 2002).*
Jin et al (Archives of Virology 138:315-330, 1994).*
Masanobu Sugimoto et al., Kokusan Ten'nento Vaccine no Aratana Yakuwari, Protein, Nucleic acid and Enzyme, Sep. 2003, pp. 1693-1701, vol. 48, No. 12.
E Mathew et al., The extracellular domain of vaccinia virus protein B5R affects plaque phenotype, extracellular enveloped virus release and intracellular actin tail formation, J.Virol., 1998, pp. 2429-2438, vol. 72, No. 3.
E Herrera et al., Functional analysis of vacinia virus B5R protein: essential role in virus envelopment is independent of a large protein of the extracellular domain., J. Virol, 1998, pp. 294-302, vol. 72, No. 1.
EJ Wolffe et al., Deletion of the vaccinia virus B5R gene encoding a 42-kilodalton membrane glycoprotein inhibits extracellular virus envelope formation and dissemination, J.Virol, 1993, pp. 4732-4741, vol. 67, No. 8.
EC Mathew et al., A mutational analysis of the vaccinia virus B5R protein, J.Gen.Virol, 2001, pp. 1199-1213, vol. 82, Pt. 5.
MM Lorenzo et al., Functional analysis of vaccinia virus B5R protein: role of the cytoplasmic tail, Virology, 1998, pp. 450-457, vol. 252, No. 2.
Engelstad, M. et al.; Virology, vol. 194, No. 2, pp. 627-637 (1993), XP 002443993.
Katz, E. et al.; Aids Research and Human Retroviruses; vol. 13, No. 17, pp. 1497-1500 (1997); XP009038314.
Boursnell, M.E.G. et al.; Vaccine, vol. 14, No. 16, pp. 1485-1494 (1996); XP 004063302.
So Hashizume, Clinical Virology, vol. 3, pp. 53-62, No. 3, (1975).

* cited by examiner

*Primary Examiner*—Mary E Mosher
(74) *Attorney, Agent, or Firm*—Birch, Stewart, Kolasch & Birch, LLP

(57) ABSTRACT

Objects of the present invention are to generate vaccine strains that undergo reversion (atavism) with difficulty and to provide smallpox vaccines with higher safety. The vaccine viruses are deficient in a part or the whole of the B5R gene of a vaccinia viral strain, LC16m8 or LC16mO, and produce no B5R gene products having normal functions. The vaccine viruses can be used as smallpox vaccines or vectors capable of expressing foreign genes. Hence, smallpox vaccines and vaccinia virus vectors are provided that produce no B5R gene products having normal functions due to reverse mutation.

18 Claims, 13 Drawing Sheets

Fig. 1

[GENETYX-MAC: Multiple Alignment]

```
B5R/m0.txt   801 GTCTGTGAAACAGATAAATGGAAATACGAAAATCCATGGAAGAAAATGTGCACAGTTTCTGATTATGTGTCTGAATTATATGATAAGCC--A-TT-ATACG   897
B5R/m8R1.txt 801 ...........................................................................G.-.-.........-   897
B5R/m8R2.txt 801 .............................................................................-.A.-.........-   897
B5R/m8R3.txt 801 ...............................................................................-.-.T....-   897
B5R/m8.txt   801 ...............................................................................-.-.-.....-   896
                  ****************************************************************************** * ** ****

B5R/m0.txt   898 AAGTGAATTCCACCATGACACTAAGTTGCAAACGGCGAAACAAATATTTCGTTGCGAAGAAAAAATGGAAATACTTCTTGGAATGATACTGTTACGTG   997
B5R/m8R1.txt 898 ................................................................................................   997
B5R/m8R2.txt 898 ................................................................................................   997
B5R/m8R3.txt 898 ................................................................................................   997
B5R/m8.txt   897 ................................................................................................   996
                  ************************************************************************************************
```

Fig. 2

```
B5R/m0.aa     1 MKTISVVTLLCVLPAVVYSTCTVPTMNNAKLTSTETSFNDKQKVTFTCDQGYHSLDPNAVCETDKWKYENPCKKMCTVSDYVSELYDKPLYEVNSTMTLS 100
B5R/m8R1.aa   1 .........................................................................................IIQ........ 100
B5R/m8R2.aa   1 .........................................................................................IIQ........ 100
B5R/m8R3.aa   1 .........................................................................................FIQ........ 100
                *****************************************************************************************   ********

B5R/m0.aa   101 CNGETKYFRCEEKNGNTSWNDTVTCPNAECQPLQLEHGSCQPVKEKYSFGEYMTINCDVGYEVIGASYISCTANSWNVIPSCQQKCDMPSLSNGLISGST 200
B5R/m8R1.aa 101 .................................................................................................... 200
B5R/m8R2.aa 101 .................................................................................................... 200
B5R/m8R3.aa 101 .................................................................................................... 200
                ****************************************************************************************************

B5R/m0.aa   201 FSIGGVIHLSCKSGFTLTGSPSSTCIDGKWNPILPTCVRSNEKFDPVDDGPDDETDLSKLSKDVVQYEQEIESLEATYHIIIVALTIMGVIFLISVIVLV 300
B5R/m8R1.aa 201 .................................................................................................... 300
B5R/m8R2.aa 201 .................................................................................................... 300
B5R/m8R3.aa 201 .................................................................................................... 300
                ****************************************************************************************************

B5R/m0.aa   301 CSCDKNNDQYKFHKLLP 317
B5R/m8R1.aa 301 ................. 317
B5R/m8R2.aa 301 ................. 317
B5R/m8R3.aa 301 ................. 317
                *****************
```

Fig. 4

| | Lister | LC16mO | LC16m8 |
|---|---|---|---|
| ts | Weak | Strong | Strong |
| Pock size | Large | Medium | Small |
| Neurotoxicity | Moderate | Very low | Very low |
| Property of proliferating in skin | Moderate | Moderate | Weak |
| Antibody production | Moderate | Strong | Moderate |

Fig. 8

Emergence frequency of RV (7 instances of serial passages in PRK cells and 2 instances of serial passages in Vero cells) as a result of serial passages □ Passaged at 30°C
▨ Passaged at 34°C

| Viral strain | RV ratio (%) |
|---|---|
| m8Δ | 0 / 0 |
| mOΔ | 0 / 0 |
| m8dTM | 0 / 0 |
| mOdTM | 0 / 0 |
| m8rc | 8.7 / 60.3 |

Fig. 9

Property of proliferating in skin in rabbit (ErD50)

| Viral strain | ErD50 (log10PFU) |
|---|---|
| m8rc | 5.83 |
| m8Δ | 5.50 |
| mOΔ | 6.00 |
| m8dTM | 4.75 |
| mOdTM | 5.00 |
| m8B5R | 1.00 |
| mO | 2.25 |

US 7,638,132 B2

HIGHLY SAFE SMALLPOX VACCINE VIRUS AND VACCINIA VIRUS VECTOR

TECHNICAL FIELD

The present invention relates to novel vaccinia viruses and virus vectors. Specifically, the present invention relates to genetically stable vaccinia viruses and vaccinia virus vectors with higher safety, which undergo reversion with difficulty because of the removal of a gene involved in reversion from an attenuated smallpox vaccinia virus LC16m8 strain or its parental LC16mO strain, which tends to undergo reversion (reverse mutation or atavism).

BACKGROUND ART

Smallpox vaccines were used in the past all over the world and contributed to the eradication of smallpox. However, all vaccine strains at that time were problematic in that 1) the strains induced serious adverse effects such as postvaccinal encephalitis and 2) it was difficult to guarantee their sterility because vaccine production was dependent on a primitive technique that involves inoculating a virus into bovine skin and then extracting the resultant from the thus-formed abscess. To address such problems, Hashizume et al., at the Chiba Serum Institute passaged a Lister strain (thought to cause relatively fewer adverse effects compared with other smallpox vaccine strains used all over the world at that time) in primary rabbit kidney (PRK) cells at 30° C. and then established an LC16 strain from the resultant as a temperature-sensitive strain that does not proliferate at temperatures of 40.8° C. or higher. The LC16 strain had greatly attenuated pathogenicity against the monkey central nervous system compared with that of the parental Lister strain, or other strains used as vaccines at that time. However, it was revealed that the proliferation property of the LC16 strain was rather elevated in rabbit skin. Accordingly, passage culture was further continued in PRK cells, so that an LC16mO strain (hereinafter also referred to as an mO strain) that forms smaller pocks was selected. Approximately 1,000 people were vaccinated with the mO strain. However, even the mO strain induce strong dermal reactions, and an LC16m8 strain (hereinafter also referred to as an m8 strain) was established as a strain that forms even smaller-sized pocks from the mO strain (So Hashizume, Clinical Virology, Vol. 3, No. 3, Jul. 1, 1975). 100,000 infants were vaccinated with the m8 strain from 1974 to 1975 without any serious adverse effects being reported. With its safety demonstrated to be higher than that of conventional vaccine strains, the m8 strain was approved as an official vaccine strain by the Ministry of Health and Welfare in Japan. Despite its weak ability to proliferate in skin compared with the mO strain, the m8 strain exhibited antibody-inducing ability at almost the same level as that of its parental Lister strain. Furthermore, the m8 strain was clearly better in terms of safety than the mO strain. Another major improvement of the m8 strain was that the strain can be produced by aseptic tissue culture using primary cultured rabbit kidney cells. However, based on applied research using the m8 strain and experience of actual production at the Chiba Serum Institute in 2001, it was shown that large plaque-forming revertants (reverse mutants) emerge during the m8 strain culture processes. It was revealed that the emergence of such revertant virus is an inevitable property of the m8 strain, since revertants also emerge from plaque-purified m8. It was also revealed that contamination with revertants may cause a concern regarding vaccine safety, since revertants' properties closely resemble those of the mO strain and their ability to proliferate in skin is elevated.

Moreover, because vaccinia viruses have a wide host range and high expression efficiency, the viruses have been used as vectors after introduction of other foreign genes (JP Patent Publication (Kohyo) No. 11-509091 A (1999)). The above LC16mO strain or LC16m8 strain has also been examined concerning its use as a vector because of its high safety.

However, as described above, the LC16mO strain is problematic in terms of property of proliferating in skin and the LC16m8 strain is problematic in terms of emergence of revertants. Thus, it has been required to generate a viral strain with higher safety as a smallpox vaccine strain or a vector virus.

DISCLOSURE OF THE INVENTION

An object of the present invention is to generate a vaccine strain that undergoes reversion (atavism) with difficulty and thus to provide a smallpox vaccine with higher safety. Another object of the present invention is to provide a vector virus for the safe expression of a foreign gene with the use of the virus.

As a result of intensive studies to achieve the above objects, the present inventors have discovered that the gene involved in reversion is the B5R gene involved in viral host range or plaque size. Specifically, the present inventors have shown that in the case of the m8 strain, the B5R gene has been deactivated because most parts of orf has been deleted as a result of frame shift due to a single base deletion in the orf. However, in revertants, the orf has been reverted as a result of insertion of a base into a new different position (FIGS. 1 and 2). The nucleotide sequence of such revertant's (RV's) B5R gene is shown in SEQ ID NO: 1 and the amino acid sequence of a B5R gene product is shown in SEQ ID NO: 2. In the mO strain, the orf of the B5R gene is complete. Hence, a recombinant virus (RVV) having such complete B5R gene was prepared (m8B5R) by cloning the B5R gene of the mO strain and then introducing the resultant into the m8 strain through homologous recombination. The RVV was screened for by selecting large plaques and then sequencing the B5R gene. Next, a construct caused to be completely deficient in terms of the whole B5R gene as well as a promoter region was prepared (ΔB5R, FIG. 6). Through homologous recombination, the deficiency of the B5R gene was introduced into m8B5R and mO strains, and RVVs (m8ΔB5R (hereinafter also referred to as m8Δ) and mOΔB5R (hereinafter also referred to as mOΔ)) were generated, respectively. Furthermore, a construct was prepared (proB5RdTM, FIG. 6) by removing a transmembrane domain of the B5R gene and then ligating the resultant to a high expression promoter PSFJ1-10. Then, this TM lacking B5R gene was introduced in the same way to m5B5R and mO to generate RVVs (m8proB5RdTM (hereinafter also referred to as m8dTM) and mOproB5RdTM (hereinafter may also be referred to as mOdTM)), respectively. The RVVs were screened for by selecting small plaques and then confirming the genome sequence.

Next, the genetic stability of the m8 strain is compared with that of the 2 types of RVVs (m8ΔB5R and mOΔB5R) wherein deficiency in the B5R gene has been introduced and that of the 2 types of RVVs (m8proB5RdTM and mOproB5RdTM) prepared by deleting the B5R gene functions and causing high expression. These viruses were passaged 7 instances in primary rabbit kidney cells at a culture temperature (30° C.) that was the same as that for production and at 34° C. Furthermore, these viruses were passaged 2 instances in Vero cells at 34° C. to facilitate detection after selective propagation of revertants. The proportions of large plaques were then measured. A re-cloned m8 strain (m8rc) was used as a control (FIG. 8). As a result, whereas in the case of m8rc, 8.7% of the virus (passage at 30° C.) and 60.3% of the virus (passage at 34° C.) formed large plaques, no large plaques were detected in the cases of these 4 types of RVVs at either temperature. When the B5R gene of large-plaque-forming clones that had emerged from m8rc was examined, recovery of orf due to mutation by insertion was confirmed in all clones.

Based on the above results, it was demonstrated that m8ΔB5R, mOΔB5R, m8proB5RdTM, and mOproB5RdTM have genetic stability that is higher than that of the m8 strain.

The present invention is as described below:

[1] a smallpox vaccine virus undergoing with difficulty reverse mutation that induces production of a B5R gene product having normal functions, which is a smallpox vaccine being deficient in a part or the whole of a B5R gene of a vaccinia virus LC16 strain, LC16m8 strain, or LC16mO strain and consisting of a vaccinia virus that produces no B5R gene products having normal functions;

[2] the smallpox vaccine virus according to [1], which is completely deficient in the B5R gene;

[3] the smallpox vaccine virus according to [1] or [2], which is deficient in a part of the B5R gene and produces no B5R gene expression products having normal functions;

[4] the smallpox vaccine virus according to any one of [1] to [3], wherein plaque sizes resulting from infection of RK13 cells with the virus and subcutaneous proliferation property resulting from administration of the virus to a rabbit are equivalent to those of the LC16m8 strain;

[5] the smallpox vaccine virus according to any one of [1] to [4], which is deficient in a part of the B5R gene, wherein a promoter is ligated upstream of the B5R gene and a part of the B5R gene is expressed, but the expression product lacks the normal functions of a B5R gene expression product;

[6] the smallpox vaccine virus according to any one of [3] to [5], which is deficient in a transmembrane domain of the B5R gene;

[7] the smallpox vaccine virus according to [5] or [6], wherein the promoter is PSFJ1-10, PSFJ2-16, or another high expression promoter for poxvirus;

[8] a smallpox vaccine virus, which consists of a vaccinia virus deficient in the whole or a part of a transmembrane domain of the B5R gene;

[9] the smallpox vaccine virus according to [8], wherein a promoter is ligated upstream of the B5R gene and a part of the B5R gene is expressed, but the expression product lacks the normal functions of a B5R gene expression product;

[10] the smallpox vaccine virus according to [8] or [9], wherein the promoter is PSFJ1-10, PSFJ2-16, or another high expression promoter for poxvirus;

[11] a smallpox vaccine pharmaceutical composition, which contains the smallpox vaccine virus according to any one of [1] to [10];

[12] a vaccinia virus vector undergoing with difficulty reverse mutation that induces production of a B5R gene product having normal functions, which is a vaccinia virus vector being deficient in a part or the whole of a B5R gene of a vaccinia virus LC16 strain, LC16m8 strain, or LC16mO strain and producing no B5R gene products having normal functions;

[13] the vaccinia virus vector according to [12], which is completely deficient in the B5R gene;

[14] the vaccinia virus vector according to [12] or [13], which is deficient in a part of the B5R gene and produces no B5R gene expression products having normal functions;

[15] the vaccinia virus vector according to any one of [12] to [14], wherein plaque sizes resulting from infection of rabbit kidney cells with the vector and subcutaneous proliferation property resulting from administration of the vector to a rabbit are equivalent to those of the LC16m8 strain;

[16] the vaccinia virus vector according to any one of [12] to [15], which is deficient in a part of the B5R gene, wherein a promoter is ligated upstream of the B5R gene and a part of the B5R gene is expressed, but the expression product lacks the normal functions of a B5R gene expression product;

[17] the vaccinia virus vector according to any one of [12] to [16], which is deficient in a transmembrane domain of the B5R gene;

[18] the vaccinia virus vector according to [16] or [17], wherein the promoter is PSFJ1-10, PSFJ2-16, or another high expression promoter for poxvirus;

[19] a vaccinia virus vector, which is deficient in the whole or a part of a transmembrane domain of a B5R gene;

[20] the vaccinia virus vector according to [19], wherein the promoter is ligated upstream of the B5R gene and a part of the B5R gene is expressed, but the expression product lacks the normal functions of a B5R gene expression product;

[21] the vaccinia virus vector according to [19] or [20], wherein the promoter is PSFJ1-10, PSFJ2-16, or another high expression promoter for poxvirus;

[22] the vaccinia virus vector according to any one of [12] to [21], which contains a foreign gene;

[23] the vaccinia virus vector according to [22], wherein the foreign gene is an antigen of a virus, a bacterium, a protozoan, or cancer; and

[24] a vaccine virus pharmaceutical composition for a virus, a bacterium, a protozoan, or cancer, which contains the vaccinia virus vector according to [23].

BRIEF DESCRIPTION OF THE DRAWINGS

FIG. 1 shows the nucleotide sequences of the B5R genes of an LC16mO strain (SEQ ID NO: 1), an LC16m8 strain, and the revertants of an LC16m8 strain.

FIG. 2 shows the amino acid sequences of the B5R gene products of the LC16mO strain (SEQ ID NO: 2, the LC16m8 strain, and the revertants of the LC16m8 strain.

FIG. 3 shows passage from a Lister strain to LC16m8.

FIG. 4 shows the features of the Lister strain, the LC16mO strain, and the LC16m8 strain.

FIG. 5 shows the plaque sizes of the LC16m8 strain, LPCs (Large Plaque Clones) that are the revertants of the LC16m8 strain, and the LC16mO strain.

FIG. 6 is a conceptual diagram showing a method for constructing a virus deficient in the B5R gene.

FIG. 7 shows photographs showing B5R protein expression in RK13 cell fractions infected with improved-type viruses as confirmed by Western blotting.

FIG. 8 shows emergence frequency of the revertants resulting from serial passages of improved-type viruses.

FIG. 9 shows improved-type viruses' property of proliferating in skin in rabbits.

BEST MODE OF CARRYING OUT THE INVENTION

Figure 3:
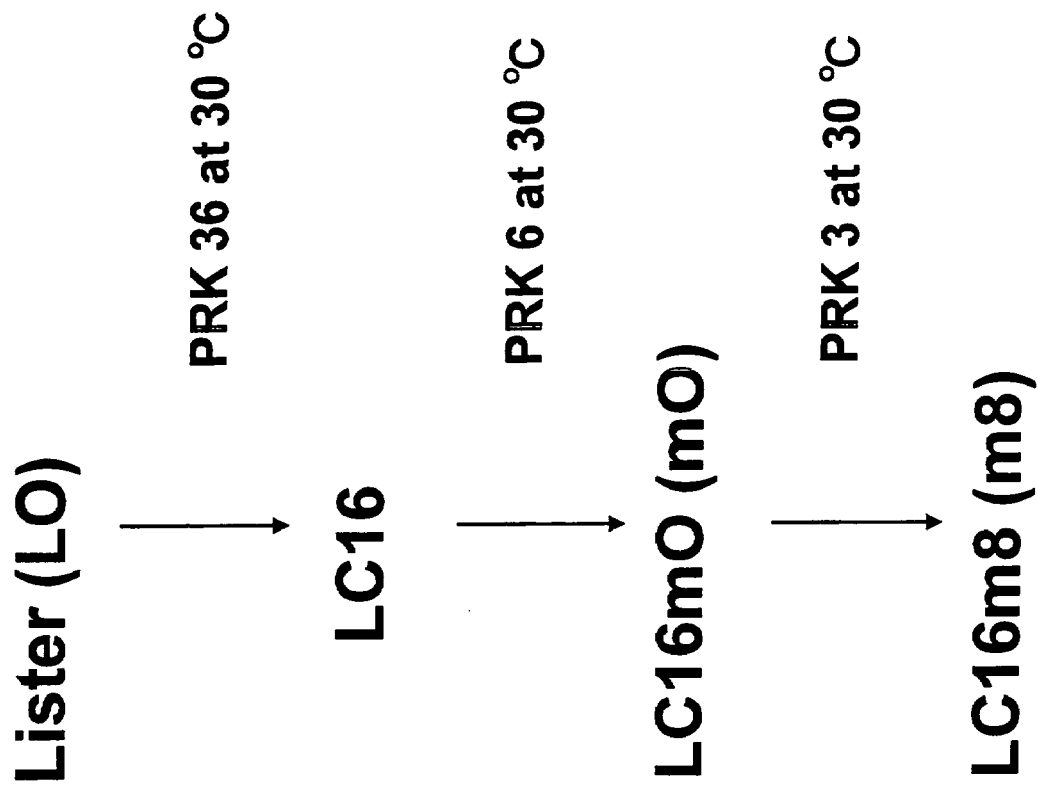

A vaccinia virus of the present invention can be generated by deleting the whole or a part of a B5R gene of a vaccinia virus such as an LC16 strain, an LC16mO strain, or an LC16m8 strain. The B5R gene encodes a protein existing in an envelope and the B5R gene product is involved in viral infection. When the B5R gene is present, property of proliferating in skin is enhanced, and therefore, the B5R gene is problematic in that it causes adverse effects such as autoinoculation when administered to a human. The LC16m8 strain produces no B5R gene products due to single-base frame shift mutation in the B5R gene, so that it has attenuated property of proliferating in skin. However, its production of the B5R gene product having normal functions will be resumed (reversion) by reverse mutation, so that there is concern over possible reversion resulting in pathogenicity.

Such vaccinia virus of the present invention is deficient in the entirety or a part of the B5R gene. Thus, the mOΔB5R strain has pathogenicity that is lower than that of the original pathogenicity of the parental LC16mO strain. In the case of m8ΔB5R, no revertants emerge by reverse mutation of the parental LC16m8 strain.

"Deficiency in the B5R gene" in the present invention means that the B5R gene is not expressed or that even if the B5R gene is expressed, the expressed protein does not retain any normal functions of the B5R gene product. This deficiency is characterized in that a deleted trait is never reverted to by point mutation in a virus and that reversion to the normal functions that have once been deleted from the B5R gene product will never take place. For example, in the case of the LC16m8 strain, one base has been deleted from the B5R gene by mutation to cause frame shift and ORF of the B5R gene has been shifted, so that normal B5R cannot be expressed. However, if one base is inserted by point mutation that takes place in the vicinity of single-base deletion portion, ORF of the B5R gene is shifted back to the original position. This makes it possible to express B5R having normal functions; that is, to cause atavism. Deficiency in the present invention includes no such deficiency that can cause atavism by point mutation. The B5R gene comprises short consensus sequences included in the region between SCR1 and SCR4 and a transmembrane (TM) domain that plays an important role in the functions of the B5R gene product. Accordingly, "deficiency in the B5R gene" may be deficiency in the transmembrane domain. Moreover, "deficiency in the B5R gene" may be deficiency not only in the transmembrane domain but also in a part of the region between SCR1 and SCR4. In this case, deficiency may be deficiency in the entirety of DNA encoding each region or deficiency such that a part of the DNA encoding each region is deleted, so that no B5R gene products having normal functions will be produced. Moreover the functional deficiency may be caused by the insertion of the foreign genes into the B5R gene region. Preferably, deficiency in the B5R gene is deficiency in the entirety of the B5R gene or deficiency in the entirety of the transmembrane domain. Furthermore, it is desirable to also delete a promoter in the B5R gene. Such deficiency can be caused by a known homologous recombination method.

Homologous recombination is a phenomenon whereby two DNA molecules mutually undergo recombination via the same nucleotide sequences within a cell. A homologous recombination method is often used for recombination of a virus such as a vaccinia virus having a huge genomic DNA. First, a plasmid (referred to as a transfer vector) is constructed by ligating a promoter to a foreign gene so that the sequence of a target vaccinia virus gene site is divided in the middle. When the resultant is introduced into cells infected with a vaccinia virus, a sequence portion of naked viral DNA in viral replication processes is replaced by a sequence portion corresponding thereto on the transfer vector. The thus-sandwiched promoter and the foreign gene are incorporated into the viral genome. For example, a plasmid, wherein the whole region of the B5R gene located between the B4R gene and the B6R gene has been deleted or a part of the B5R gene has been deleted is prepared as a transfer vector by cloning a region between the B4R gene and the B6R gene of a vaccinia virus into a plasmid. The thus prepared plasmid is introduced into cells infected with a vaccinia virus. Examples of cells that may be infected with a vaccinia virus include BSC-1 cells, HTK-143 cells, Hep2 cells, MDCK cells, Vero cells, HeLa cells, CV1 cells, COS cells, RK13 cells, BHK-21 cells, and primary rabbit kidney cells. A vector can be introduced into cells by a known method such as a calcium phosphate method, a cationic liposome method, or an electroporation method. To facilitate identification of a recombinant, a gene (e.g., a B5R gene, a HA gene, or a TK gene) that can be a selection marker is often used as a gene (of an introduction site) that is divided by homologous recombination so as to lose its functions. A transfer vector is designed and/or prepared based on the nucleotide sequence information of a vaccinia virus gene. The gene to be disrupted is subjected to homologous recombination using the transfer vector. Such transfer vector can be prepared according to a method described in "DNA Cloning 4—Mammalian System—($2^{nd}$ ed.)" (edited by D. M. Glover et al.; translation supervised by Ikunoshin Kato, TaKaRa) or the like. As a method for selecting homologous recombinants that have undergone homologous recombination, a selection method using plaque size (in the case of the B5R gene), the presence or the absence of hemadsorption in plaques (in the case of HA gene), resistance to a BudR drug (in the case of TK gene), or the like may be used, depending on the selected target gene. Alternatively, either a PCR method or a Southern blotting method can also be used.

Figure 5:
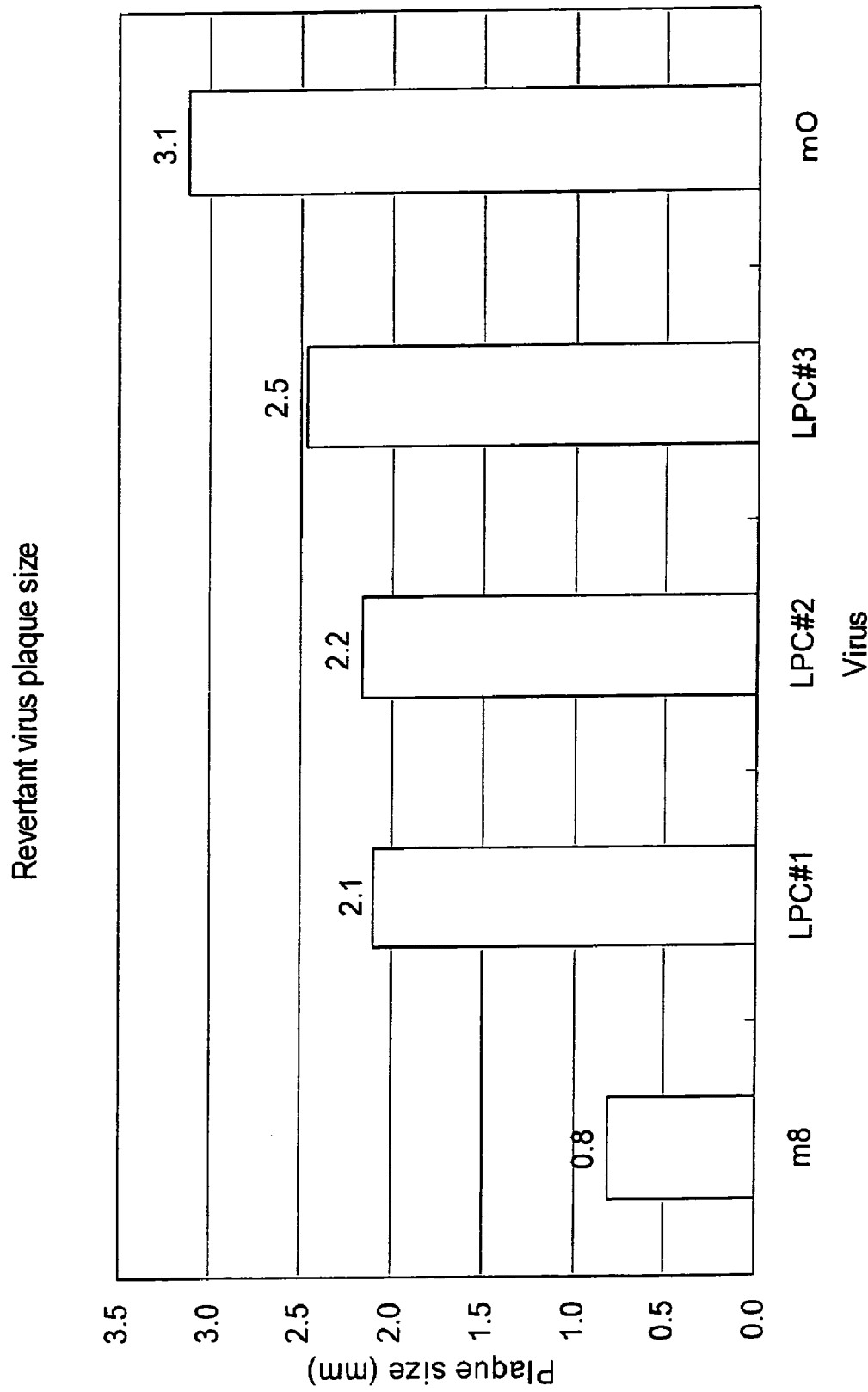
Figure 10A:
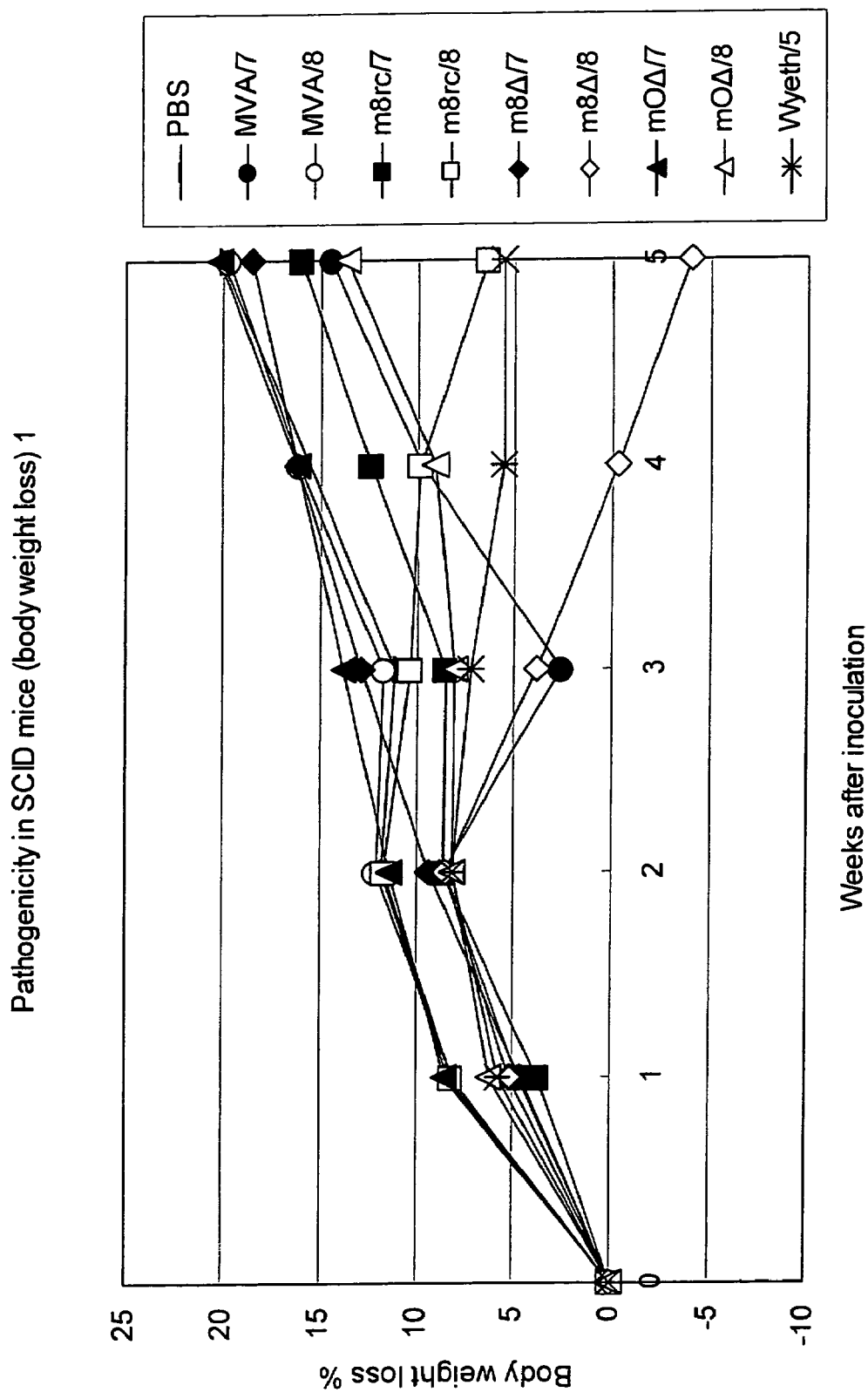
FIG. 10A shows body-weight losses in SCID mice to which viruses were administered.
Figure 10B:
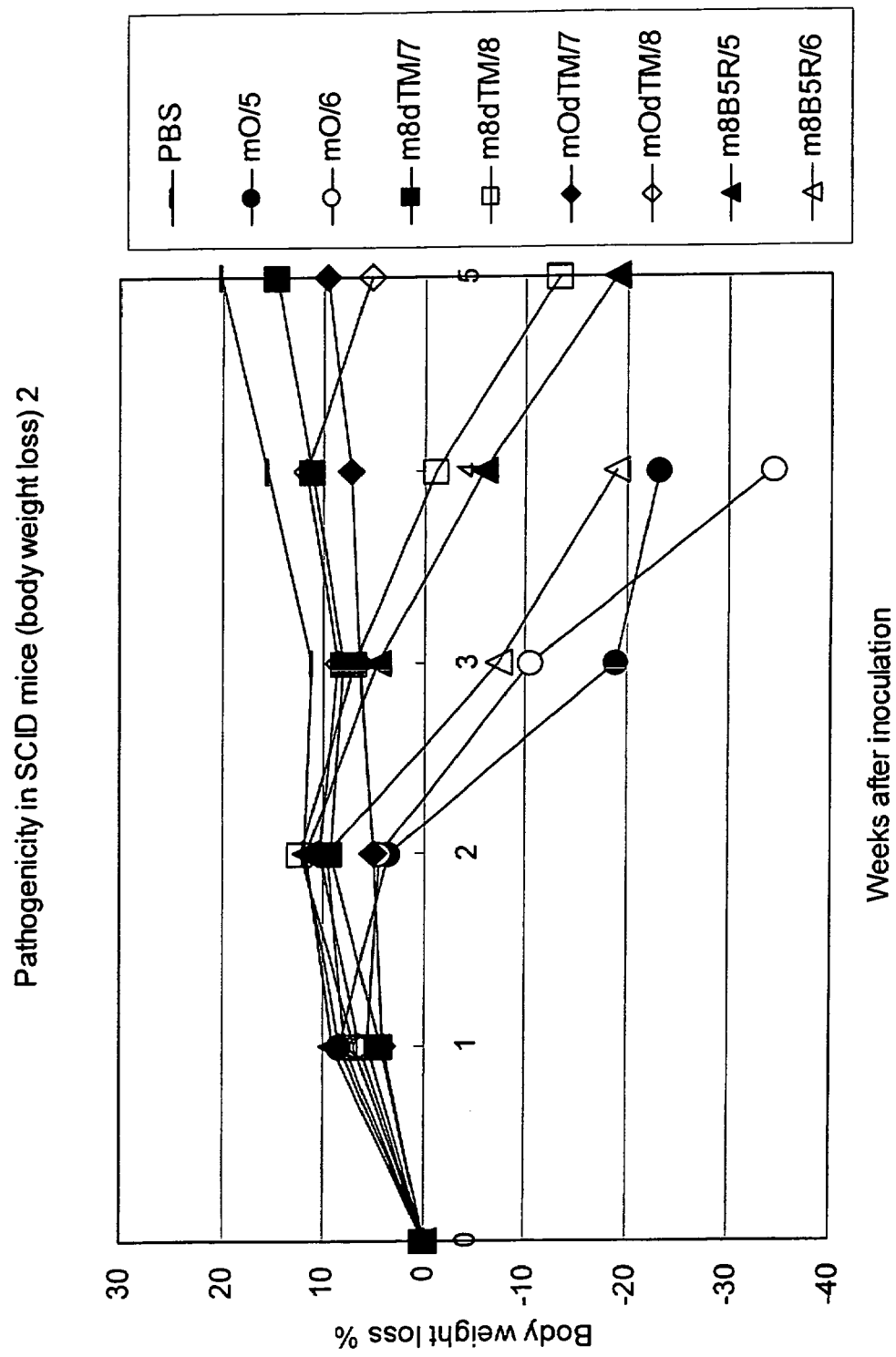
FIG. 10B shows body-weight losses in SCID mice to which viruses were administered.
Figure 11:
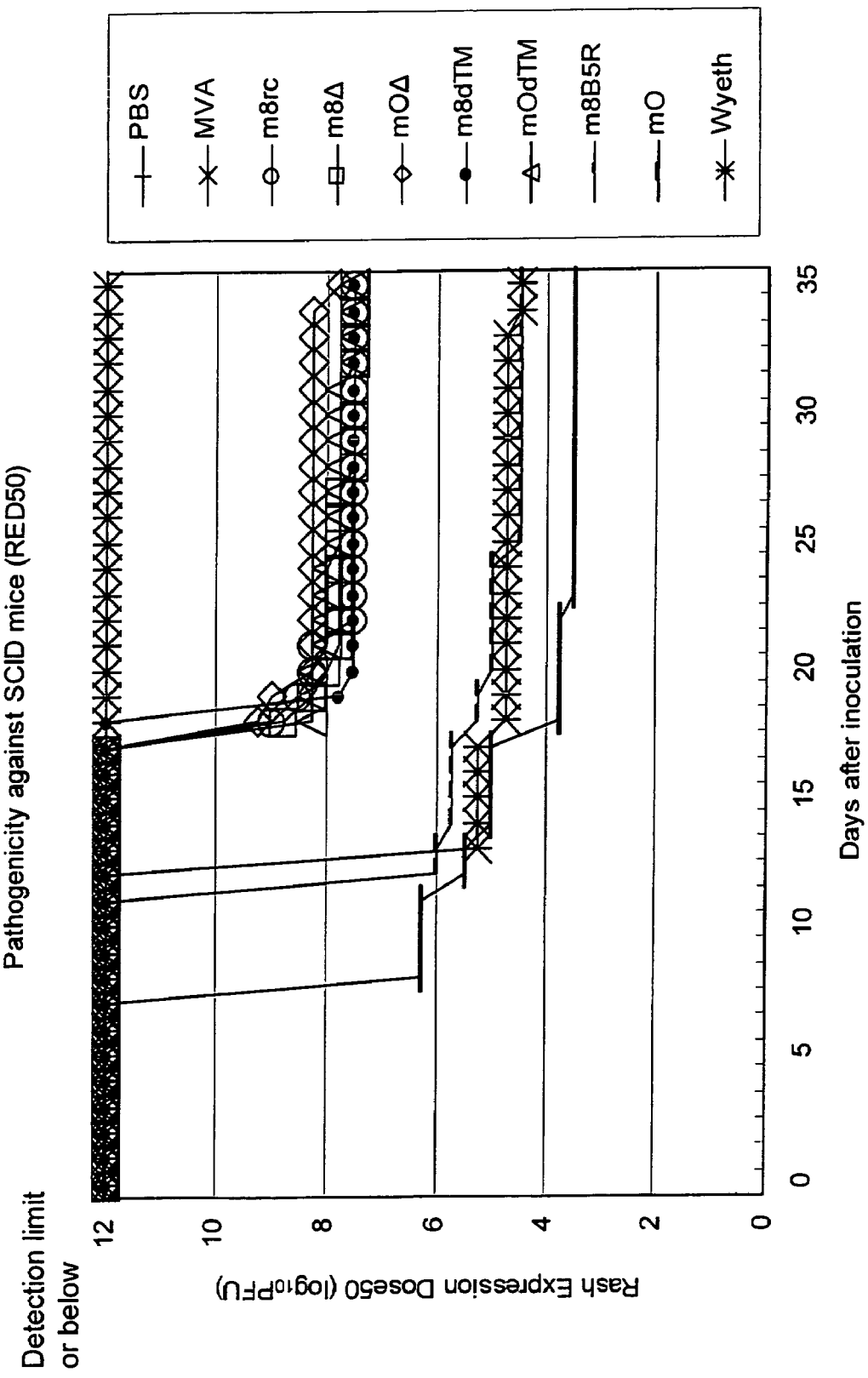
FIG. 11 shows changes over time in RED50 in SCID mice to which viruses were administered.

The B5R gene product is present on the surfaces of infected cells and viral envelopes, functions to enhance infection efficiency at the time of infection and/or transmission of the virus to adjacent cells or other sites within a host body, and is also involved in viral plaque size and host range. For example, deletion of the B5R gene results in smaller plaque sizes when animal cells such as RK13 cells are infected with the virus, and it results in smaller pock sizes on the chorioallantois of an embryonated egg. Furthermore, the proliferation property of the virus is significantly lowered in Vero cells. Furthermore, the ability to proliferate in skin of the virus is lowered when the virus is intradermally administered to a rabbit, so that the skin pathogenicity of the virus is lowered. Accordingly, whether or not a B5R protein lacks its functions can be determined using sizes of pocks and plaques formed when RK13 cells are infected with a virus, the proliferation property of a virus in Vero cells, the skin pathogenicity of a virus in rabbits, and the like as indices. Moreover, the gene sequence of a vaccinia virus may also be examined. In the case of the vaccinia virus of the present invention, compared with the Lister strain or the LC16mO strain having B5R gene functions, the resulting plaque sizes and pock sizes are smaller when animal cells are infected with the virus. Furthermore, the proliferation property of the virus in Vero cells, the skin pathogenicity of the virus, and the like are also lowered. Compared with the LC16m8 strain, however, the resulting plaque sizes and pock sizes when animal cells are infected with the virus are equivalent to those of the LC16m8 strain. Furthermore, the proliferation property of the virus in rabbit kidney cells, the proliferation property of the virus in Vero cells, the subcutaneous pathogenicity of the virus, and the like are also equivalent to those of the LC16m8 strain. FIG. 5 shows the plaque sizes when rabbit kidney cells were infected with the LC16mO strain and the LC16m8 strain. FIG. 9 shows the property of proliferating in skin in rabbits of the LC16mO strain and that of the LC16m8 strain (re-cloned LC16m8 strain). Moreover, the deletion of the B5R gene also results in the reduced pathogenicity of the virus when animals are inoculated with the virus. For example, viruses are intraperitoneally inoculated into SCID mice and then the mouse body weights are measured over time. In the case of a viral strain producing the B5R gene product having normal functions, pock formation is observed approximately 2 weeks after inoculation with $10^5$ PFU of the virus, and the mice begin to lose their body weights. However, in the case of a viral strain producing no B5R gene products having normal functions, no pock formation is observed, even after inoculation with $10^7$ PFU of the virus, and no body-weight loss is observed. Furthermore, when the pathogenicity in the case of inoculation into animals is examined using RED50 (viral load that can cause pock formation in half of the animals) as an index, a viral strain producing the B5R gene product having normal functions shows a value that is 2 or more logs lower than that of a viral strain producing no B5R gene products having normal functions. FIG. 10A, FIG. 10B, and FIG. 11 show pathogenicity against SCID mice. "B5R gene product (s) having normal functions" in the present invention means gene products that have functions that are the same as those of the gene product encoded by a wild-type B5R gene and also have the above property.

Figure 12:
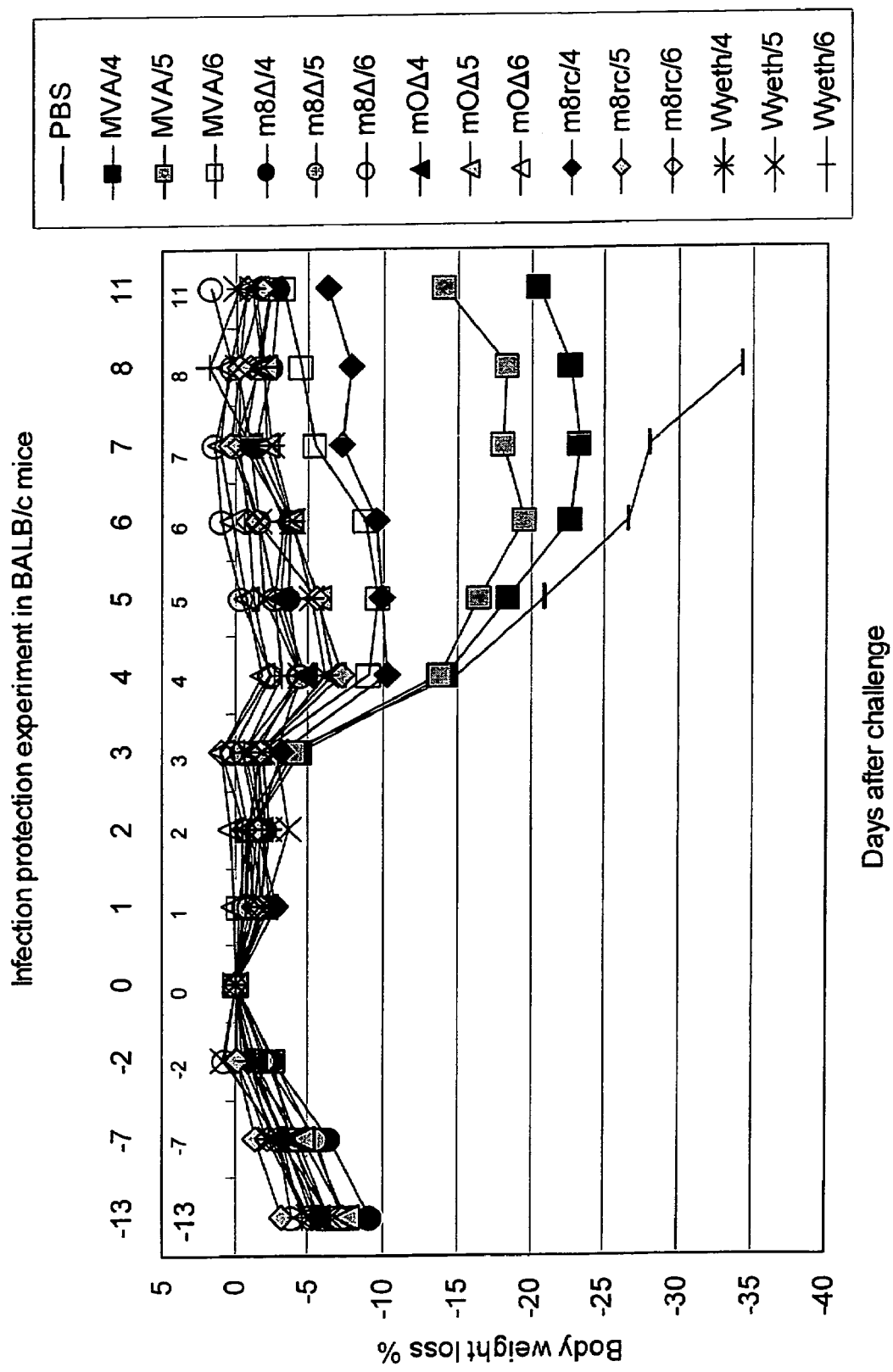
FIG. 12 shows body-weight losses in BALB/c mice challenged with a virulent vaccinia virus.

Furthermore, viral strains completely deficient in the B5R gene are comparable to viral strains having the B5R gene in terms of phylactic ability, as in the results shown in FIG. 12. It has also been reported that a B5R gene product is important as a protective antigen for anti-smallpox vaccines. Hence, when such B5R gene product is used as a smallpox vaccine, it may be preferable that a part of such B5R gene product be produced. Therefore, in the vaccinia virus of the present invention, the B5R gene may also be expressed while maintaining the antigenicity of its expression product but lacking its normal functions. For this purpose, a virus may be designed so that a part of the B5R gene, such as a part or the whole of the region between SCR1 and SCR4, is expressed. To further enhance the antigenicity of a vaccine, a virus may also be designed so that such region is expressed in a greater amount. For this purpose, a high expression promoter may be operatively linked upstream of the partially deficient B5R gene. Examples of a promoter that is used herein include a PSFJ1-10 promoter, a PSFJ2-16 promoter, and other high expression promoters for poxvirus (e.g., a p7.5K promoter, a p11K promoter, a T7.10 promoter, a CPX promoter, a HF promoter, a H6 promoter, and a T7 hybrid promoter).

In the present invention, the LC16mO strain and the LC16m8 strain that are completely deficient in the B5R gene are referred to as mOΔB5R and m8ΔB5R, respectively, or may also be referred to as mOΔ and m8Δ, respectively. The high-expression LC16mO strain and LC16m8 strain that are obtained by deletion of a transmembrane domain of the B5R gene followed by ligation of a promoter upstream of the B5R gene are referred to as mOproB5RdTM and m8proB5RdTM, respectively, or may also be referred to as mOdTM and m8dTM, respectively.

The LC16mO strain was generated from the Lister strain via the LC16 strain and the LC16m8 strain was further generated from the LC16mO strain (Protein Nucleic Acid and Enzyme, Vol. 48 No. 12 (2003), pp. 1693-1700). The LC16m8 strain is isolated from the Lister strain by steps as shown in FIG. 2. The LC16mO strain and the LC16m8 strain can be obtained from the Chiba Prefectural Institute of Public Health.

The LC16mO strain and the LC16m8 strain of the present invention, which are deficient in the B5R gene, can be used as safe smallpox virus vaccines without undergoing reversion.

Furthermore, the present invention encompasses a vaccinia virus vector comprising the above LC16 strain, LC16mO strain, or LC16m8 strain, which is deficient in the B5R gene.

A desired foreign gene can be introduced into the vector. With the use of the above homologous recombination technique, theoretically, the foreign gene can be introduced into any site of the vaccinia virus genome. Homologous recombination may be performed by the above method. For example, a plasmid (transfer vector) is prepared by ligating a foreign gene (to be introduced) to a DNA sequence (corresponding to a site into which the gene is introduced). The thus prepared plasmid is introduced into a cell infected with a vaccinia virus. Examples of a transfer vector that can be used herein include pSFJ1-10, pSFJ2-16, pMM4, pGS20, pSC11, pMJ601, p2001, pBCB01-3, pBCB06, pTKgpt-F1-3s, pTM1, pTM3, pPR34, pPR35, pgpt-ATA18-2, and pHES1-3. A region into which the foreign gene is introduced is located within the gene that is not essential for the life cycle of a vaccinia virus. Examples of such gene include a hemagglutinin (HA) gene, a thymidine kinase (TK) gene, and an F fragment. Moreover, the foreign gene may also be introduced into the above B5R gene region (between the B4R gene and the B6R gene). The gene into which such foreign gene is introduced is preferably the gene, the deletion of which causes a change in a viral trait and thus facilitates selection of a recombinant. For example, in the case of the HA gene, a recombinant prepared by introduction of a foreign gene into the HA gene loses its functions because the HA gene is divided by the introduced foreign gene. Accordingly, the resulting plaques look white, since adsorption of chicken erythrocytes stops, so that a recombinant can be easily selected. Furthermore, a recombinant prepared by introduction of the foreign gene into the TK gene loses the functions of the TK gene and 5-bromodeoxyuridine (BudR) does not act lethally. Thus, the recombinant can be selected using BudR. Moreover, a recombinant prepared by introduction of the foreign gene into the B5R gene forms smaller plaques. Thus, the recombinant can be selected based on such plaque size. Examples of cells that can be used herein, that is, can be infected with a vaccinia virus, include Vero cells, HeLa cells, CV1 cells, COS cells, RK13 cells, BHK-21 cells, primary rabbit kidney cells, BSC-1 cells, HTK-143 cells, Hep2 cells, and MDCK cells.

Furthermore, when the foreign gene is introduced, it is desirable to operatively link an appropriate promoter upstream of the foreign gene. Examples of such promoter that can be used herein are not limited and include the above PSFJ1-10, PSFJ2-16, a p7.5K promoter, a p11K promoter, a T7.10 promoter, a CPX promoter, a HF promoter, a H6 promoter, and a T7 hybrid promoter. A method for introducing the foreign gene into a vaccinia virus vector of the present invention can be performed by a known method for constructing a recombinant vaccinia virus vector. Such method can be performed according to Experimental Medicine, The Protocol Series, Experimental Protocols for Gene Transfer & Expression Analysis (Idenshi Donyu & Hatsugen Kaiseki Jikken-ho), Separate Volume, edited by Izumi Saito et al., YODOSHA CO., LTD. (issued on Sep. 1, 1997) or DNA Cloning 4—Mammalian System—($2^{nd}$ ed.), edited by D. M. Glover et al., translation supervised by Ikunoshin Kato, TaKaRa, EMBO Journal (1987, vol. 6, pp. 3379-3384), for example.

As described above, the foreign gene can be produced with the use of a vaccinia virus vector into which the foreign gene has been introduced. At this time, an appropriate host cell is infected with such vaccinia virus vector having the foreign gene introduced therein, and then the host cell is cultured. The various above animal cells can be used as host cells. Culture may be performed under known culture conditions for animal cells.

Furthermore, through introduction of genes encoding antigens of viruses, bacteria, protozoans, cancer, and the like as foreign genes, the thus obtained vaccinia virus vectors into which such foreign genes have been introduced can be used as vaccines against such various forms of viruses, bacteria, protozoans, cancer, and the like. For example, the gene encoding a protective antigen (neutralizing antigen) of human immunodeficiency virus, hepatitis virus, herpesvirus, mycobacteria, Plasmodium, severe acute respiratory syndrome (SARS) virus, or the like or a gene encoding a cancer antigen may be introduced. The present invention also encompasses vaccinia virus vectors into which these antigens have been introduced.

Moreover, the present invention encompasses a smallpox vaccine pharmaceutical composition containing the vaccinia virus of the present invention that is deficient in the B5R gene, the use of such vaccinia virus of the present invention that is deficient in the B5R gene as a smallpox vaccine, and a method for protecting against smallpox infection, which comprises administering such vaccinia virus to a subject.

Administration methods, doses, and the like for the vaccine pharmaceutical composition of the present invention are similar to those for known vaccinia virus vaccines that have already been used as vaccines. The vaccine pharmaceutical composition of the present invention contains the vaccinia virus vaccine of the present invention in a pharmaceutically effective dose as an active ingredient. The composition may be in the form of a sterile aqueous or nonaqueous solution, a suspension, or an emulsion. Moreover, the composition may also contain a pharmaceutically acceptable diluent (e.g., a salt, a buffer agent, or an adjuvant), an auxiliary agent, a carrier, or the like. The vaccine pharmaceutical composition of the present invention may be administered via various perenteral routes such as subcutaneous, intravenous, intradermal, intramuscular, intraperitoneal, intranasal, and percutaneous routes. Of these, intradermal administration is preferable. A pharmaceutically effective dose is an amount that is sufficient to result in a desired biological effect. Specifically, such dose that is employed in this case is an amount that is sufficient for obtaining at least either a cell-mediated immune response or a humoral immune response to a virus antigen. An effective dose can be appropriately determined depending on age, sex, health condition, body weight, and the like of a subject. Examples of such effective dose include, but are not limited to, approximately $10^2$ to $10^{10}$ pock-forming units (PFUs) or plaque-forming units (PFUs) and preferably $10^5$ to $10^6$ pock-forming units (PFUs) or plaque-forming units (PFUs) per administration for a human adult.

Furthermore, the present invention encompasses a vaccinia virus vaccine pharmaceutical composition that is a vaccinia virus vector that is deficient in the B5R gene and contains a foreign gene introduced therein, where the introduced foreign gene encodes an antigen of a virus, a bacterium, a protozoan, or cancer and the use of the vaccine. The present invention further encompasses a method for protecting against or treating viral infection, bacterial infection, protozoan infection, cancer, or the like, which comprises administering the vector to a subject. The method for administering the vaccine pharmaceutical composition and the dose for the same may be employed according to those employed for the above smallpox vaccine pharmaceutical composition.

Next, the present invention will be further described specifically by referring to examples.

Example 1

Construction of Mutant Deficient in B5R Gene and High-Expression Recombinant Partially Deficient in B5R Construction of Transfer Vector (pB4R+B6R) for Deficiency in B5R Gene TA Cloning for B4R The B4R gene was amplified using the purified genomic DNA of an m8 strain as a template and two primers (GATGCTGTTGTGCTGTGTTTGC (SEQ ID NO: 3) and GTTAACACTGTCGAGCACTAAAAGG (SEQ ID NO: 4)), and an Hpa I site was introduced on the 3' side of orf. The resultant was cloned into a TA vector (pCR II)(pB4R+Hpa I). After confirmation of the nucleotide sequence of pB4R+Hpa I, the whole region of the B4R gene and a multicloning site of the TA vector were amplified using the resulting nucleotide sequence as a template and two primers (GATGCTGTTGTGCTGTGTTTGC (SEQ ID NO: 5) and TTGTGTGGAATTGTGAGCGGA (SEQ ID NO: 6)). After purification of the PCR product, both ends were blunt-ended using T4 DNA polymerase (B4R+HpaI fragment).

TA Cloning for B6R

The B6R gene was amplified using the purified genomic DNA of an m8 strain as a template and two primers (GTTAACGTTCCATAAATTGCTACCG (SEQ ID NO: 7) and GTGTGACCTCTGCGTTGAATAG (SEQ ID NO: 8)), and an Hpa I site was introduced on the 5' side of orf. The resultant was cloned into a TA vector (pB6R+Hpa I).

Ligation of B4R to B6R

After confirmation of the nucleotide sequence of pB6R+Hpa I, the sequence was digested with Hpa I followed by dephosphorylation with BAP. Next, the resultant was mixed with the B4R+Hpa I fragment for ligation. A region formed of parts of the thus ligated B4R gene and B6R gene was amplified using the mixture as a template and primers ps/hr-s1 (TCGGAAGCAGTCGCAAACAAC (SEQ ID NO: 9) and ps/hr-as1 (ATACCATCGTCGTTAAAAGCGC (SEQ ID NO: 10)). The PCR product was cloned into a TA vector and then the nucleotide sequence was confirmed (pB4R+B6R).

Construction of Transfer Vector (pB4R+B6R proB5RdTM) for High-Expression Recombinant Partially Deficient in B5R Only an ectodomain region (between SCR1 and SCR4) of the B5R gene was amplified using the purified genomic DNA of the mO strain as a template and two primers (ATGAAAACGATTTCCGTTGTTACG (SEQ ID NO: 11) and TCAATGATAAGTTGCTTCTAACGA (SEQ ID NO: 12)).

The resultant was cloned into a TA vector (pB5RdTM). After confirmation of the nucleotide sequence of pB5RdTM, the sequence was cleaved with a restriction enzyme Pst I, blunt-ended with T4 DNA polymerase, and then cleaved with Sac I. Thus, a B5RdTM fragment was excised. The B5RdTM fragment was ligated to a transfer vector pSFJ1-10 that had been digested with Sma I and Sac I (pSFJdTM). Next, pSFJdTM was digested with Hpa I and Sac I and then a promoter+B5RdTM fragment (proB5RdTM) was excised. The fragment was ligated to pB4R+B6R that had been digested with Hpa I and Sac I (pB4R+B6R proB 5RdTM).

Preparation of Recombinant Virus

RK13 cells or PRK cells cultured to 80% confluency in 35 mm dishes were infected with vaccinia viruses (an m8 strain in the case of m8B5R, m8B5R in the cases of m8Δ and m8proB5RdTM, and an mO strain in the cases of mOΔ and mOproB5RdTM) at a moi of 0.02. After 1 hour of adsorption at room temperature, transfer vector plasmid DNAs (pB5R in the case of m8B5R, pB4R+B6R in the cases of m8Δ and mOΔ, and pB4R+B6R proB5RdTM in the cases of m8proB5RdTM and mOproB5RdTM) that had been mixed with LipofectAMINE PLUS (Invitrogen) were added to and incorporated by cells according to the manual. The cells were cultured at 34° C. for 2 days. After freezing and thawing of the cells, the cells were sonicated. The resultant was appropriately diluted and then inoculated into RK13 cells that had almost reached confluency. 0.8% methyl cellulose-containing Eagle MEM with 5% FCS media were added, followed by 2 to 3 days of culture at 34° C. Neutral red was added to the media to a final concentration of 0.01%. After staining of the cells at 34° C. for 3 hours, the media were removed and then the cell surfaces were washed twice with a phenol red-free Eagle MEM medium. In the case of m8B5R, large plaques were collected by scraping off the plaques with a chip head. In the cases of m8Δ, m8proB5RdTM, mOΔ, and mOproB5RdTM, small plaques were collected by scraping off the plaques using a chip head. The thus obtained plaques were suspended in Eagle MEM media. After sonication of the suspensions of the thus collected plaques, 200 μL of each suspension was centrifuged at 15,000 rpm for 30 minutes. 50 μL of sterilized and distilled water or 10 mM Tris-HCl (pH7.5) was added to each precipitate. After 30 seconds of sonication, each resultant was heated at 95° C. for 10 minutes, thereby extracting genomic DNA. The thus obtained DNA was subjected to screening by PCR. PCR was performed using ps/hr-s1 and ps/hr-as1 in the cases of m8Δ and mOΔ or using ps/hr-s1 and B5R793as (GATCCGAAGAAT-GATATCCC) (SEQ ID NO: 13) in the cases of m8proB5RdTM and mOproB5RdTM. For clones for which PCR products of a predetermined size had been detected, the nucleotide sequences of all PCR products were confirmed by direct sequencing. Clones having no problems in terms of nucleotide sequence were selected and then subjected to 2 to 3 instances of plaque purification using RK13 cells. All viruses were cultured in large amounts using RK13 cells, purified and concentrated by ultra centrifugation using 35(W/V)% sucrose cushion, subjected to viral titer measurement in RK13 cells, and then subjected to the experiments.

Figure 6:
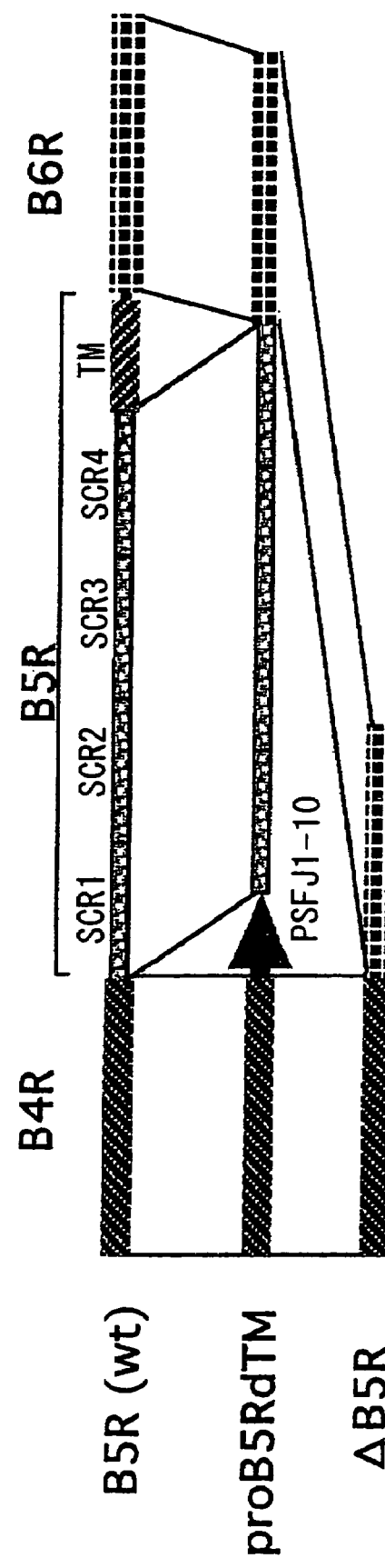

FIG. 6 shows construction of a virus deficient in the B5R gene.

Example 2

Figure 7A:
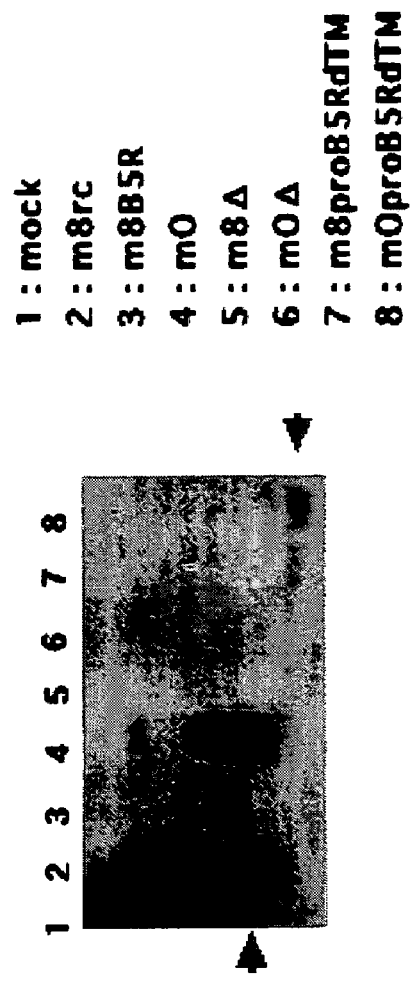

Confirmation of B5R Protein Expression in Mutant Deficient in B5R Gene and High-Expression Recombinant Partially Deficient in B5R RK13 cells were infected with 4 types of improved-type viruses (m8Δ, mOΔ, m8proB5RdTM, and mOproB5RdTM) at a moi of 10. B5R protein expression in infected cell fractions was confirmed on day 1 after infection by Western blotting (FIG. 7a). An anti-B5R rat monoclonal antibody (recognizing an SCR2 region) was used as a primary antibody in Western blotting. Specific bands were detected using an ECL Western Blotting Detection System (Amersham Biosciences K.K.).

In the cases of m8B5R (prepared by introducing a wild-type B5R gene into an m8 strain) and mO strains, B5R protein bands with the same molecular weight were confirmed. In improved-type viruses of high-expression type, (m8proB5RdTM and mOproB5RdTM), the expression of a short B5R product was confirmed. In the cases of m8rc (re-cloned m8 strain), m8Δ, and mOΔ, no B5R gene products were detected (FIG. 7a).

Figure 7B:
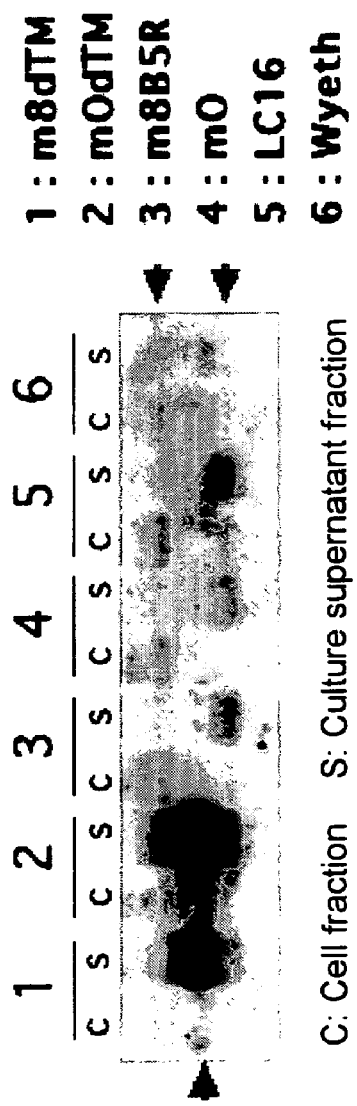

Furthermore, to detect B5R proteins secreted in culture supernatants, cells were infected with m8proB5RdTM, mOproB5RdTM, m8B5R, mO, LC16, and Wyeth strains, respectively, under the same culture conditions described above. The culture supernatants were concentrated using 12.5% TCA and then subjected to confirmation by Western blotting (FIG. 7b). An anti-B5R rabbit polyclonal antibody was used as a primary antibody. Detection was performed using an ECL Plus Western Blotting Detection System (Amersham Biosciences K.K.). Each cell fraction was applied in an amount that was one-fortieth of the amount of entire fraction and each culture supernatant was applied in an amount that was one-tenth of the amount of entire supernatant.

In the cases of m8proB5RdTM and mOproB5RdTM expressing a B5R protein lacking a TM domain, such B5R protein was detected in larger amounts in culture supernatant fractions than in cell fractions. In the cases of other viral strains, a B5R protein with a small molecular weight (approximately 35 Kd) was detected in culture supernatant fractions in amounts comparable to those in cell fractions.

Example 3

Confirmation of Emergence Frequency of Revertant 4 types of improved-type viruses (m8Δ, mOΔ, m8proB5RdTM, and mOproB5RdTM) were serially passaged 7 instances in PRK (cells for production) under conditions of moi=1.0 and 30° C. or 34° C. The viruses were serially passaged 2 instances in Vero cells at 34° C. The presence or the absence of the emergence of revertants was confirmed by measuring RV contents. Revertant contents were obtained by calculating the ratio of a viral titer in Vero cells to a viral titer in RK13 cells. A recloned m8 strain (m8rc) was used as a control. FIG. 8 shows the emergence frequencies of the revertants.

Even after 7 instances of serial passage of the 4 types of the improved-type viruses in PRK cells followed by selective propagation of revertants in Vero cells, no revertants emerged. Thus, it was demonstrated that these 4 virus types undergo reversion with difficulty.

On the other hand, revertants were detected from the recloned m8 strain (m8rc). In the case of m8rc, such revertants had already emerged in the first generation of serial passages in PRK cells upon selective propagation of revertants in Vero cells. Thus, it was revealed that the m8 strain easily undergoes reversion.

Example 4

Property of Proliferating in Skin of Improved-Type Viruses in Rabbits

A rabbit skin inoculation test was conducted for improved-type viral strains (m8Δ, mOΔ, m8proB5RdTM, and mOproB5RdTM). Specifically, ErD50 (Erythema Dose 50: a viral load that can cause erythemas of 1 cm or greater over 50% of an inoculation site) was measured and then the property of proliferating in skin was evaluated. As controls, an mO strain, m8rc, and m8B5R prepared by introducing a wild-type B5R gene into an m8 strain were used.

Hair on the backs of Japanese White rabbits each having a body weight of 3.5 kg or more was cut, and then the skin was completely dehaired with barium sulfide. On the next day, 10-fold serial dilutions (0.1 mL each) of the viruses were intradermally inoculated into the backs. Each rabbit was subjected to inoculation with two serial dilution series of a virus, one of which was inoculated from the shoulder towards the rump and the other of which was inoculated in the opposite direction, from high to low doses. Two rabbits (4 inoculations/dose) were used for each sample. Erythema diameters within inoculation sites were measured every day for 7 days after inoculation. Erythemas that were greater than 10 mm were determined to be positive. Based on each reaction at the time when erythemas reached their peak, ErD50 was calculated by the Reed and Muench method. FIG. 9 shows property of proliferating in skin in rabbits.

It was shown that whereas the viral strains (m8B5R and mO strains) having the B5R gene retaining activity had strong ability to proliferate in skin and showed low ErD50 values (1.00 and 2.25), B5R gene-deficient viral strains (m8rc, m8Δs, and mOΔ) had lowered ability to proliferate in skin and showed higher ErD50 values (5.83, 5.50, and 6.00). Thus, it was supported that the B5R gene is directly involved in property of proliferating in skin. Recombinants (m8proB5RdTM and mOproB5RdTM) expressing TM domain-deficient B5R also showed ErD50 values (4.75 and 5.00) higher than those shown by the control viral strains (m8B5R and mO) expressing wild-type B5R. Thus, it was shown that in the cases of such recombinants, property of proliferating in skin was significantly attenuated at the same level as in the cases of m8rc, m8Δ, and mOΔ.

Example 5

Infection Experiment in SCID Mice

Six-week-old BALB/cSCID mice (female, 4 mice per group) were inoculated intraperitoneally with $10^7$ PFU/dose to $10^9$ PFU/dose of m8Δ, mOΔ, m8dTM, or mOdTM strain. Body-weight loss and the presence or the absence of the onset of infection were observed for 5 weeks after inoculation. Similar observation was performed on control groups, including: a group inoculated with PBS; a group inoculated with $10^7$ PFU/dose to $10^9$ PFU/dose of an MVA strain that can undergo one-step growth alone in mammalian cells; a group inoculated with $10^7$ PFU/dose to $10^9$ PFU/dose of a recloned m8 strain (m8rc); a group inoculated with $10^4$ PFU/dose to $10^6$ PFU/dose of an mO strain; a group inoculated with $10^4$ PFU/dose to $10^6$ PFU/dose of m8B5R constructed by incorporating the B5R gene of the mO strain into an m8 strain; and a group inoculated with $10^3$ PFU/dose to $10^5$ PFU/dose of a vaccine strain (Wyeth strain) that is currently used in the U.S.A. (FIG. 10A, FIG. 10B, and FIG. 11).

FIG. 10A and FIG. 10B show body-weight losses in mice. Among groups separately inoculated with the m8Δ, the mOΔ, the m8dTM, and the mOdTM strains, groups inoculated at $10^8$ PFU/dose showed slight body-weight losses. However, groups inoculated at $10^7$ PFU/dose showed almost no body-weight losses and no onset similar to those of a group inoculated with PBS or MVA. In contrast, among groups inoculated with the mO strain, the m8B5R strain, and the Wyeth strain each having B5R gene activity, pock formation began 2 weeks after inoculation even in groups inoculated at $10^5$ PFU/dose. Furthermore, body weight loss began along with the start of pock formation. Particularly in groups inoculated with the mO strain, most mice died within 4 weeks after inoculation at any dose.

As an index for the pathogenicity of viral strains against SCID mice in addition to body weight loss, Rash Expression Dose 50 (RED50), which is the viral load required to cause pock formation in 50% of the mice, was defined. FIG. 11 shows changes over time in RED50. As a result, 5 strains (m8Δ, mOΔ, m8dTM, mOdTM, and m8rc) deficient in the B5R gene functions all showed almost the same values, which were 2 or more logs higher than those for the 3 strains (mO, m8B5R, and Wyeth) having B5R activity. Moreover, timing (at which pock formation began) for the 5 strains differed by few days from that of the 3 strains. No onset or body-weight losses were observed in groups inoculated with these 5 strains at $10^7$ PFU/dose, which is 10 to 100 times greater than the inoculation dose that is generally administered to a human body. Hence, the high safety of these strains was demonstrated.

Example 6

Protection of BALB/c Mice

To evaluate the protective immunogenicity of m8Δ and mOΔ strains as smallpox vaccines, protection of BALB/c mice against virulent vaccinia has been examined. Six-week-old BALB/c mice (female, 8 mice per group) were vaccinated intramuscularly with each viral strain at $10^4$ PFU/dose to $10^6$ PFU/dose. Four weeks after vaccination, the mice were challenged intranasally with a virulent strain (Western Reserve (WR) strain) of vaccinia virus at a lethal dose ($10^6$ PFU/dose). Body weight loss was measured after the challenge (FIG. 12). The current vaccine strain, Wyeth, in the U.S.A., m8rc, and MVA were used as controls.

Although the mice vaccinated with m8Δ and mOΔ strains, like those with the Wyeth strain, were observed to transiently lose their body-weight on day 4 after challenge at any doses, the they were completely resistant to the challenge and none of them died. On the other hand, among groups vaccinated with the MVA strain, particularly groups inoculated with $10^4$ PFU and $10^5$ PFU of the strain, their severe body-weight losses were observed and significant body-weight losses were also observed in a group inoculated with $10^6$ PFU of the strain. Two mice of a group inoculated with $10^4$ PFU of the strain died. It was confirmed by these results that the m8Δ strain and the mOΔ strain are both provided with immunogenicity that is comparable to those of current smallpox vaccines.

INDUSTRIAL APPLICABILITY

The present invention enables to the provision of smallpox vaccine viruses with higher safety and having attenuated pathogenicity, such as attenuated property of proliferating in skin, that undergo reversion with difficulty. This makes it possible to endure process management for producing smallpox vaccines, which provides a large advantage in vaccine production. Moreover, the supply of safe smallpox vaccines with stable quality is important in national risk management. Furthermore, the use of such vaccinia viruses as recombinant live vaccines or expression vector systems is approaching a practical level, in addition to applications with regard to smallpox vaccines. Such viruses can also be tools that are important for the development of vaccines, diagnostic agents, or the like against emerging and reemerging infectious diseases. Hence, improvement in the m8 strain has great significance also in terms of application.

All publications, patents, and patent applications cited herein are incorporated herein by reference in their entirety. Furthermore, a person skilled in the art would easily understand that various modifications of and changes to the present invention are feasible within the technical idea and the scope of the invention as disclosed in the attached claims. The present invention is intended to encompass such modifications and changes.

The invention claimed is:

1. A vaccinia virus generated from a vaccinia virus LC16 strain, LC16m8 strain or LC16mO strain undergoing with difficulty reverse mutation that induces production of a B5R gene product having normal functions, which is a vaccinia virus being deficient in a part or the whole of a B5R gene of a vaccinia virus LC16 strain, LC16m8 strain, or LC16mO strain and consisting of a vaccinia virus that produces no B5R gene products having normal functions.

2. The vaccinia virus according to claim 1, which is completely deficient in the B5R gene.

3. The vaccinia virus according to claim 1, which is deficient in a part of the B5R gene and produces no B5R gene expression products having normal functions.

4. The vaccinia virus according to claim 1, wherein plaque sizes resulting from infection of RK13 cells with the virus and subcutaneous proliferation property resulting from administration of the virus to a rabbit are equivalent to those of the LC16m8 strain.

5. The vaccinia virus according to claim 1, which is deficient in a part of the B5R gene, wherein a promoter is ligated upstream of the B5R gene and a part of the B5R gene is expressed, but the expression product lacks the normal functions of a B5R gene expression product.

6. The vaccinia virus according to claim 3, which is deficient in a transmembrane domain of the B5R gene.

7. The vaccinia virus according to claim 5, wherein the promoter is PSFJ1-10, PSFJ2-16, or another high expression promoter for poxvirus.

8. A smallpox vaccine, which contains the vaccinia virus according to claim 1.

9. A vaccinia virus vector generated from a vaccinia virus LC16 strain, LC16m8 strain, or LC16mO strain, undergoing with difficulty reverse mutation that induces production of a B5R gene product having normal functions, which is a vaccinia virus vector being deficient in a part or the whole of a B5R gene of a vaccinia virus LC16 strain, LC16m8 strain, or LC16mO strain and producing no B5R gene products having normal functions.

10. The vaccinia virus vector according to claim 9, which is completely deficient in the B5R gene.

11. The vaccinia virus vector according to claim 9, which is deficient in a part of the B5R gene and produces no B5R gene expression products having normal functions.

12. The vaccinia virus vector according to claim 9, wherein plaque sizes resulting from infection of rabbit kidney cells with the vector and subcutaneous proliferation property resulting from administration of the vector to a rabbit are equivalent to those of the LC16m8 strain.

13. The vaccinia virus vector according to claim 9, which is deficient in a part of the B5R gene, wherein a promoter is ligated upstream of the B5R gene and a part of the B5R gene is expressed, but the expression product lacks the normal functions of a B5R gene expression product.

14. The vaccinia virus vector according to claim 11, which is deficient in a transmembrane domain of the B5R gene.

15. The vaccinia virus vector according to claim 13, wherein the promoter is PSFJ1-10, PSFJ7-16 or another high expression promoter for poxvirus.

16. The vaccinia virus vector according to claim 9, which contains at least one foreign gene.

17. The vaccinia virus vector according to claim 16, wherein the foreign gene is an antigen of a virus, a bacterium, a protozoan, or cancer.

18. A pharmaceutical composition for a virus, a bacterium, a protozoan, or cancer, which contains the vaccinia virus vector according to claim 17.

* * * * *

SEQUENCE LISTING

<160> NUMBER OF SEQ ID NOS: 13

<210> SEQ ID NO 1
<211> LENGTH: 197
<212> TYPE: DNA
<213> ORGANISM: Vaccinia virus

<400> SEQUENCE: 1

```
gtctgtgaaa cagataaatg gaaatacgaa aatccatgca agaaaatgtg cacagtttct    60
gattatgtct ctgaattata tgataagcca ttatacgaag tgaattccac catgacacta   120
agttgcaacg gcgaaacaaa atattttcgt tgcgaagaaa aaaatggaaa tacttcttgg   180
aatgatactg ttacgtg                                                  197
```

<210> SEQ ID NO 2
<211> LENGTH: 317
<212> TYPE: PRT
<213> ORGANISM: Vaccinia virus

<400> SEQUENCE: 2

```
Met Lys Thr Ile Ser Val Val Thr Leu Leu Cys Val Leu Pro Ala Val
  1               5                  10                  15

Val Tyr Ser Thr Cys Thr Val Pro Thr Met Asn Asn Ala Lys Leu Thr
                 20                  25                  30

Ser Thr Glu Thr Ser Phe Asn Asp Lys Gln Lys Val Thr Phe Thr Cys
             35                  40                  45

Asp Gln Gly Tyr His Ser Leu Asp Pro Asn Ala Val Cys Glu Thr Asp
         50                  55                  60

Lys Trp Lys Tyr Glu Asn Pro Cys Lys Lys Met Cys Thr Val Ser Asp
 65                  70                  75                  80

Tyr Val Ser Glu Leu Tyr Asp Lys Pro Leu Tyr Glu Val Asn Ser Thr
                 85                  90                  95

Met Thr Leu Ser Cys Asn Gly Glu Thr Lys Tyr Phe Arg Cys Glu Glu
            100                 105                 110

Lys Asn Gly Asn Thr Ser Trp Asn Asp Thr Val Thr Cys Pro Asn Ala
        115                 120                 125

Glu Cys Gln Pro Leu Gln Leu Glu His Gly Ser Cys Gln Pro Val Lys
    130                 135                 140

Glu Lys Tyr Ser Phe Gly Glu Tyr Met Thr Ile Asn Cys Asp Val Gly
145                 150                 155                 160

Tyr Glu Val Ile Gly Ala Ser Tyr Ile Ser Cys Thr Ala Asn Ser Trp
                165                 170                 175

Asn Val Ile Pro Ser Cys Gln Gln Lys Cys Asp Met Pro Ser Leu Ser
            180                 185                 190

Asn Gly Leu Ile Ser Gly Ser Thr Phe Ser Ile Gly Gly Val Ile His
        195                 200                 205

Leu Ser Cys Lys Ser Gly Phe Thr Leu Thr Gly Ser Pro Ser Ser Thr
    210                 215                 220

Cys Ile Asp Gly Lys Trp Asn Pro Ile Leu Pro Thr Cys Val Arg Ser
225                 230                 235                 240
```

-continued

```
Asn Glu Lys Phe Asp Pro Val Asp Asp Gly Pro Asp Asp Glu Thr Asp
                245                 250                 255

Leu Ser Lys Leu Ser Lys Asp Val Val Gln Tyr Glu Gln Glu Ile Glu
            260                 265                 270

Ser Leu Glu Ala Thr Tyr His Ile Ile Ile Val Ala Leu Thr Ile Met
        275                 280                 285

Gly Val Ile Phe Leu Ile Ser Val Ile Val Leu Val Cys Ser Cys Asp
    290                 295                 300

Lys Asn Asn Asp Gln Tyr Lys Phe His Lys Leu Leu Pro
305                 310                 315

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 3
gatgctgttg tgctgtgttt gc                                            22

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 4
gttaacactg tcgagcacta aaagg                                         25

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 5
gatgctgttg tgctgtgttt gc                                            22

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 6
ttgtgtggaa ttgtgagcgg a                                             21

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 7
gttaacgttc cataaattgc taccg                                         25
```

```
<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 8
gtgtgacctc tgcgttgaat ag                                          22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 9
tcggaagcag tcgcaaacaa c                                           21

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 10
ataccatcgt cgttaaaagc gc                                          22

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 11
atgaaaacga tttccgttgt tacg                                        24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 12
tcaatgataa gttgcttcta acga                                        24

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:Synthetic
      DNA

<400> SEQUENCE: 13
gatccgaaga atgatatccc                                             20
```